US00PP12470P2

(12) United States Plant Patent
Cosner et al.

(10) Patent No.: US PP12,470 P2
(45) Date of Patent: Mar. 19, 2002

(54) IMPATIENS PLANT NAMED 'TIRE'

(76) Inventors: Harlan B. Cosner; Susan L. Cosner, both of P.O. Box 173, Broadbent, OR (US) 97414

( * ) Notice: Subject to any disclaimer, the term of this patent is extended or adjusted under 35 U.S.C. 154(b) by 0 days.

(21) Appl. No.: 09/535,086

(22) Filed: Mar. 23, 2000

(30) Foreign Application Priority Data

Mar. 30, 1999 (CA) ..... 99-1617

(51) Int. Cl.[7] ..... A01H 5/00
(52) U.S. Cl. ..... Plt./317
(58) Field of Search ..... Plt./317, 319

(56) References Cited

U.S. PATENT DOCUMENTS

PP3,919 P * 6/1976 Hope et al. ..... Plt./317
PP11,550 P * 10/2000 Jonkers ..... Plt./317

OTHER PUBLICATIONS

UPOV–ROM GTITM Computer Database, 2000/06, GTI Jouve Retrieval Software, citation for 'TiRe'.*

* cited by examiner

*Primary Examiner*—Bruce R. Campell
*Assistant Examiner*—Susan B. McCormick
(74) *Attorney, Agent, or Firm*—Bradley M. Ganz, Esq.

(57) ABSTRACT

A new and distinct cultivar of *Impatiens walleriana* plant named 'TiRe', characterized by large red fully double flowers, flowers that are positioned above or beyond the foliage, good heat tolerance, dark green foliage and mounded, freely branching and dense plant habit.

1 Drawing Sheet

BACKGROUND—FIELD OF INVENTION

The present invention relates to a new and distinct cultivar botanically known as *Impatiens walleriana*, and by the cultivar name 'TiRe'.

The cultivar of the photograph was developed and selected in a controlled breeding program in a controlled environment in Coquille, Oreg. by the inventors, Harlan Cosner and Sue Cosner, as described herein.

BACKGROUND—DESCRIPTION OF THE PRIOR ART

The closest known cultivar of prior art is named 'Salsa Red', subject of U.S. Plant Pat. No. 9,606.

COMPARISON

The impatiens plant of the present invention differs from prior plants, namely, Salsa Red in at least the following ways:

1. The flowers of the present invention have brighter color than 'Salsa Red'; and 2. The 'Salsa Red' impatiens plant often has flowers that have deformed centers, while the impatiens plants of the present cultivar have much better flower form with fewer deformities.

These and other characteristics will be apparent to persons skilled in the art.

BACKGROUND—DISCOVERY

The present cultivar was developed by standard cross-pollination. Its seed parent is a semi-double impatiens plant with red flowers. This plant was designated B-9X-31 under the inventors' controlled breeding program. The pollen parent is a pollen-producing double impatiens plant with red flowers. This plant was designated B-9X-13 under the inventors' controlled breeding program. The parent plants are not the subject of any granted or pending application. The cross was made in the inventors' controlled breeding program, and the first asexual reproduction was made at Broadbent, Oreg. Successive asexually reproduced generations have shown the present invention to be stable. Each asexually reproduced generation has been accomplished using lateral stems with leaves.

The traits of the cultivar of the present invention that have been observed in each successive generation of asexual reproduction and which are unique are the large bright red male and female sterile fully double flowers, flowers that are positioned above or beyond the foliage, good heat tolerance, dark green foliage and mounded, freely branching and dense plant habit.

Color references are according to The Royal Horticultural Society Colour Chart, except where general terms of ordinary dictionary signficance are used.

DETAILED DESCRIPTION

The following observations, measurements and description of the plants and flowers are based on the environmental and cultural practices at Coquille, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM of two successive feedings followed by one leaching with clear water. Plants started in the last week of June and finished in late September. The light levels were 4,000 to 6,000 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph illustrates the overall appearance and the flower color of the cultivar of the present invention described herein. The photograph was taken of a mature plant 14 weeks old during full inflorescence. There may be variations between the colors in the photograph and the colors in the following description due to light reflectance, or the amount of blue or red light captured in the film. If such variations occur, the written description shall control.

Parentage: The new cultivar was developed by standard cross-pollination. As noted above, its seed parent was a semi-double with large red flowers; its pollen parent was a pollen-producing double with red colored flowers.

Propagation:

*Type cutting.*—Lateral stems with leaves were the cuttings used for asexual reproduction.

*Time to initiate roots.*—Approximately 7 to 14 days at 72° F. soil temperature.

Appearance and form of plant:

*Plant form and habit.*—Mounded, with a medium vigorous, dense and bushy growing habit. A free branching habit.

*Plant size.*—Height is about 20 cm and width is about 40 cm.

*Root description.*—The rooting habit is characterized by numerous, fibrous and well-branched roots.

*Branching habit.*—Plants are self-branching. Stems are strong and freely produced. The number of stems depends upon cultural practices, age of stems used as cuttings and the number of growth buds present on the cutting when stuck. The observed plant's average stem length is about 20 cm. Each stem generally produces about three laterals.

*Stems.*—Diameter is about 0.7 cm. Internode length is about 2 cm. Color is 146B with darker markings that that are hard to distinguish due to their small size but appear close to 183C or 187C. The observed plant's stem texture is smooth.

*Foliage.*—Leaves are simple, generally symmetrical, abundant, alternate and flat. Shape is ovate with attenuate base, acuminate apex, and crenate margin. Texture is smooth and satiny. The observed plant's leaf venation pattern is similar to other plants having similar leaf shapes, with single veins branching upwardly off from the central, longitudinal axis of each leaf, along the length of the axis, toward the margin of the leaf and forming an acute angle relative to the axis.

*Foliage size.*—Size of the largest leaves is about 6.5 cm in length, and 4.5 cm in width.

*Foliage color.*—Adaxial color is closest to 147A, venation color 147B; abaxial color is 147B with darker markings close to 177A, venation color 148A.

*Petioles.*—Petiole shape is half round with a flat upper surface measuring about 3 mm wide, about 2 mm in depth, and about 1.5 cm in length. Color on the top is 148B with reddish hard to determine markings which appear close to 178B. Bottom color is 146C.

*Flower size.*—Diameter of about 5.2 cm, and depth of about 2 cm.

*Flower texture.*—The flower texture is smooth and satiny.

*Flower count.*—Flowers per stem usually number about 12 to 15 from visible buds to open flowers at a time during the flowering period.

*Flower fragrance.*—No discernible fragrance.

*Natural flowering season.*—Year around under greenhouse conditions, and the frost-free period from spring through fall outdoors.

*Duration of flowering.*—Continuous throughout the flowering season.

*Time to flower.*—About six weeks from a rooted cutting.

*Bud.*—Ovate shape with length of about 1.2 cm, width of about 1 cm and depth of about 1 cm. Color of top is 143C with reddish markings that are hard to determine due to their small size but appear close to 172A to 172B. Bottom color is 142C to 142D.

*Petal size and shape.*—Shape is obovate to exaggerated obovate, cuneate base, entire margin, obtuse to retuse apex. Usually two petals fused at base comprise the largest petals, each being about 2 cm wide and 2.7 cm long.

*Petal color.*—Adaxial is 42A, with abaxial color is 44D.

*Petal count.*—Numerous, generally 25 or more.

*Spur.*—Shape is acicular tapering tube, usually curved. Color at apex is 183B fading close to 178B at sepal with a greenish tint that is hard to determine, but which appear close to 199A to 199B. Length is about 3.25 cm and width at base is about 2 mm.

*Calyx.*—The calyx consists of a single sepal. The sepal shape is obovate, acuminate to acute apex, obtuse base and entire margin. Length is about 1.5 cm and width is about 0.7 cm. Adaxial color is 142D with center blotch close to 60C; abaxial color is 142C to 142D.

*Peduncles.*—Length is about 2.25 cm and diameter is about 2 mm. Color is 146B to 146C with small hard to determine streaks close to 178B. Peduncles have a smooth texture.

*Pedicels.*—Usually numbering 2 or 3, each having a length of about 2.5 cm and diameter of about 1.5 mm. Color is 146C with reddish hard to determine streaks close to 178B. Pedicels have a smooth texture.

*Reproductive organs.*—The plants of the new cultivar are both male and female sterile. No reproductive organs have been found to exist.

*Disease resistance.*—'TiRe' has shown good resistance to botrytis.

*Rooting ability.*—Easy, no hormones are needed.

*Cold/heat resistance.*—'TiRe' and 'Salsa Red' were grown side by side under shade cloth in Alva, Fla.

during late spring through July. The outdoor temperatures were in the 90° F.+ degree temperature range. 'Salsa Red' did not branch as well as 'TiRe'. The flowers of 'Salsa Red' had many unformed petaloids resulting in flowers that tended to look single to semi-double, and the flower color was less intense than the flower color of 'TiRe'. The flower shape of 'TiRe' was also without noticeable deformities.

What is claimed:

1. A new and distinct cultivar of *Impatiens walleriana* plant as illustrated and as described herein.

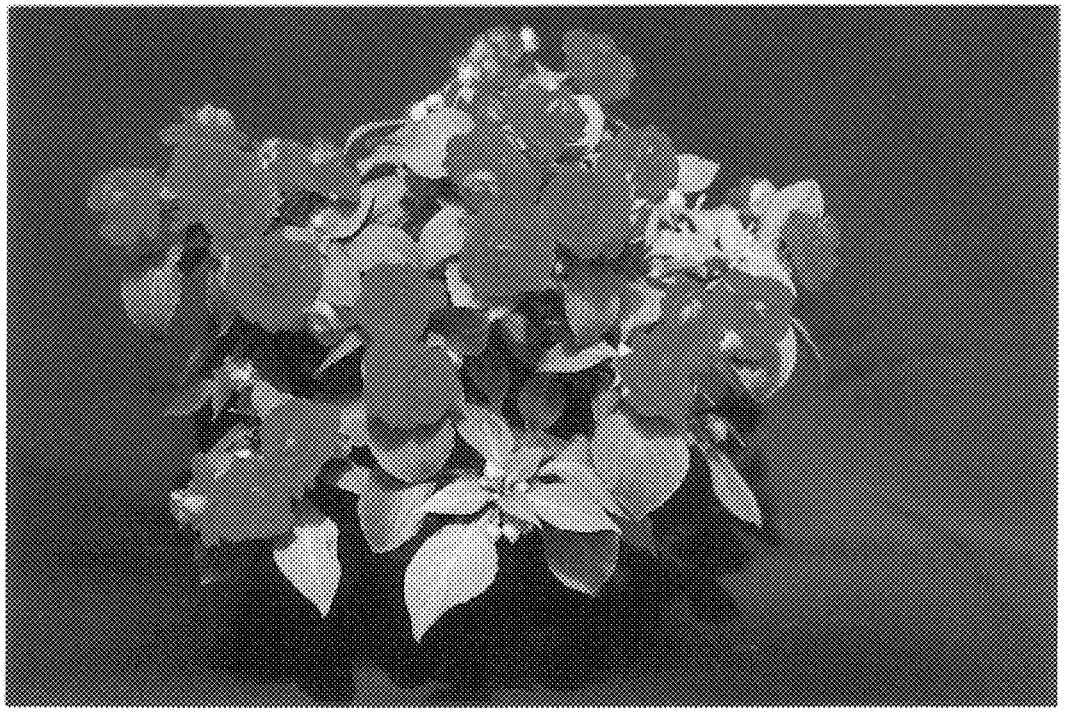

* * * * *